United States Patent
Tseng et al.

(10) Patent No.: US 11,793,851 B2
(45) Date of Patent: Oct. 24, 2023

(54) METHOD FOR TREATING A SIDE EFFECT CAUSED BY BCG PERFUSION THERAPY FOR BLADDER CANCER

(71) Applicant: Chen-Yu Lee, Taipei (TW)

(72) Inventors: Hsuan-Ching Tseng, New Taipei (TW); Da-Tong Ju, Taipei (TW); Sung-Sen Yang, Taipei (TW); Wei-Te Cheng, New Taipei (TW); Chen-Yu Lee, Taipei (TW); Yan-Chih Liao, Taipei (TW)

(73) Assignee: Chen-Yu Lee, Taipei (TW)

( * ) Notice: Subject to any disclaimer, the term of this patent is extended or adjusted under 35 U.S.C. 154(b) by 281 days.

(21) Appl. No.: 17/010,883

(22) Filed: Sep. 3, 2020

(65) Prior Publication Data

US 2022/0062364 A1 Mar. 3, 2022

(51) Int. Cl.

| | |
|---|---|
| *A61K 36/515* | (2006.01) |
| *A61P 1/14* | (2006.01) |
| *A61K 36/744* | (2006.01) |
| *A61K 36/232* | (2006.01) |
| *A61K 36/64* | (2006.01) |
| *A61K 36/71* | (2006.01) |
| *A61K 36/233* | (2006.01) |
| *A61K 36/68* | (2006.01) |
| *A61K 36/284* | (2006.01) |
| *A61K 36/884* | (2006.01) |
| *A61K 36/484* | (2006.01) |
| *A61K 36/899* | (2006.01) |
| *A61K 36/65* | (2006.01) |
| *A61K 36/488* | (2006.01) |
| *A61K 36/708* | (2006.01) |
| *A61K 36/734* | (2006.01) |
| *A61K 35/57* | (2015.01) |
| *A61P 13/10* | (2006.01) |
| *A61P 13/02* | (2006.01) |
| *A61P 25/00* | (2006.01) |
| *A61K 36/539* | (2006.01) |

(52) U.S. Cl.
CPC ............ *A61K 36/515* (2013.01); *A61K 35/57* (2013.01); *A61K 36/232* (2013.01); *A61K 36/233* (2013.01); *A61K 36/284* (2013.01); *A61K 36/484* (2013.01); *A61K 36/488* (2013.01); *A61K 36/539* (2013.01); *A61K 36/64* (2013.01); *A61K 36/65* (2013.01); *A61K 36/68* (2013.01); *A61K 36/708* (2013.01); *A61K 36/71* (2013.01); *A61K 36/734* (2013.01); *A61K 36/744* (2013.01); *A61K 36/884* (2013.01); *A61K 36/899* (2013.01); *A61P 1/14* (2018.01); *A61P 13/02* (2018.01); *A61P 13/10* (2018.01); *A61P 25/00* (2018.01)

(58) Field of Classification Search
None
See application file for complete search history.

(56) References Cited

FOREIGN PATENT DOCUMENTS

| | | | |
|---|---|---|---|
| CN | 103055100 A | * | 4/2013 |
| CN | 104524275 A | * | 4/2015 ............. A61K 33/12 |

OTHER PUBLICATIONS

CN-103055100-A translated doc (Year: 2013).*
CN-104524275-A translated doc (Year: 2015).*
Zhang (Radix Puerariae : An overview of Its Chemistry, Pharmacology, Pharmacokinetics, and Clinical Use, Journal of Chemical Pharmacology, vol. 53, Issue 8, pp. 787-877, Aug. 2013). (Year: 2013).*
Hong (Liver Cancer Treatments by Chinese Medicines and their Active Compounds, Anti-Cancer Drugs, Nature, Synthesis and Cell, Dec. 7, 2016) (Year: 2016).*
Lightin (https://www.lightinfortune.com/info-detail/crataegi-fructusgives-you-a-good-appetite). (Year: 2019).*
Xuan-Jing Zeng et al., "Case Report on Chinese medicine medicinal treatment of urothelial carcinoma recurrence following transurethral resection of bladder tumor with adjuvant intravesical bacillus Calmette-Guerin and complications", JCMAS, vol. 7, No. 1, Dec. 2019, pp. 147-156.

* cited by examiner

*Primary Examiner* — Terry A McKelvey
*Assistant Examiner* — Jacob A Boeckelman
(74) *Attorney, Agent, or Firm* — BACON & THOMAS, PLLC

(57) ABSTRACT

The present invention relates to a method for treating a side effect caused by bacillus Calmette-Guérin (BCG) perfusion therapy for bladder cancer. The method includes: administering a Chinese medicine composition to a subject in need thereof; wherein the Chinese medicine composition is an extract of a first mixture comprising *Gentiana scabra*, *Scutellariae Radix*, *Gardeniae Fructus*, *Angelicae Sinensis Radix*, *Rehmanniae radix*, *Akebiae Caulis*, *Bupleurum chinense*, *Plantaginis Semen*, *Atractylodes lancea*, *Rhizoma alismatis*, and *Glycyrrhiza uralensis*.

21 Claims, No Drawings

METHOD FOR TREATING A SIDE EFFECT CAUSED BY BCG PERFUSION THERAPY FOR BLADDER CANCER

BACKGROUND OF THE INVENTION

1. Field of the Invention

The present invention relates to a method for treating a side effect caused by Calmette-Guérin (BCG) perfusion therapy for bladder cancer. Specifically, the present invention relates to a method for treating side effects, including red and swollen bladder lining and hematuria, caused by Calmette-Guérin (BCG) perfusion therapy for bladder cancer.

2. Description of Related Art

According to the American Cancer Society, bladder cancer is the fourth most common cancer in men. Bladder cancer refers broadly to various malignant tumors from the bladder, including urothelial carcinoma, also known as transitional cell carcinoma (TCC), squamous cell carcinoma, adenocarcinoma, sarcoma, small cell carcinoma, and the like. Among them, urothelial carcinoma is the most common.

At present, surgery is mainly used to treat bladder cancer. The initial treatment is to scrape the tumor through endoscopic curettage, combined with chemotherapy drugs or bacille Calmette-Guérin (BCG) perfusion therapy, to reduce the recurrence of bladder cancer. The BCG perfusion therapy damages endothelial cells of the bladder using treated bacteria of BCG, thereby stimulating the patient's own immunity to eliminate tumor cells.

However, common side effects of BCG perfusion therapy include hematuria, fever, wound in bladder lining and pain. Therefore, there is a need to provide a treatment method to treat, ameliorate or alleviate the side effects induced by BCG perfusion therapy for bladder cancer.

SUMMARY OF THE INVENTION

In view of this, the present invention provides a Chinese medicine composition and treatment method that can treat, ameliorate or alleviate a side effect caused by bacillus Calmette-Guérin (BCG) perfusion therapy for bladder cancer.

One object of the present invention is to provide a Chinese medicine composition for treating a side effect caused by bacillus Calmette-Guérin (BCG) perfusion therapy for bladder cancer, wherein the Chinese medicine composition is an extract of a first mixture comprising *Gentiana scabra*, *Scutellariae Radix*, *Gardeniae Fructus*, *Angelicae Sinensis Radix*, *Rehmanniae radix*, *Akebiae Caulis*, *Bupleurum chinense*, *Plantaginis Semen*, *Atractylodes lancea*, *Rhizoma alismatis*, and *Glycyrrhiza uralensis*.

Another object of the present invention is to provide a method for treating a side effect caused by bacillus Calmette-Guérin (BCG) perfusion therapy for bladder cancer, comprising: administering a Chinese medicine composition to a subject in need thereof. Specifically, an effective amount of said Chinese medicine composition is administered to the subject in need thereof.

In the present invention, the first mixture may comprise 1-5 parts by weight of *Gentiana scabra*, 1-13 parts by weight of *Scutellariae Radix*, 1-8 parts by weight of *Gardeniae Fructus*, 1-5 parts by weight of *Angelicae Sinensis Radix*, 1-5 parts by weight of *Rehmanniae radix*, 1-5 parts by weight of *Akebiae Caulis*, 1-5 parts by weight of *Bupleurum chinense*, 1-5 parts by weight of *Plantaginis Semen*, 2-6 parts by weight of *Atractylodes lancea*, 2-11 parts by weight of *Rhizoma alismatis*, and 3-7 parts by weight of *Glycyrrhiza uralensis*. Preferably, the first mixture may comprise 2-4 parts by weight of *Gentiana scabra*, 2-12 parts by weight of *Scutellariae Radix*, 2-7 parts by weight of *Gardeniae Fructus*, 2-4 parts by weight of *Angelicae Sinensis Radix*, 2-4 parts by weight of *Rehmanniae radix*, 2-4 parts by weight of *Akebiae Caulis*, 2-4 parts by weight of *Bupleurum chinense*, 2-4 parts by weight of *Plantaginis Semen*, 3-5 parts by weight of *Atractylodes lancea*, 3-10 parts by weight of *Rhizoma alismatis*, and 4-6 parts by weight of *Glycyrrhiza uralensis*.

In one embodiment of the present invention, the first mixture may further comprise *Typhae pollen*.

In one aspect of the present invention, the first mixture may comprise 1-5 parts by weight of *Gentiana scabra*, 1-5 parts by weight of *Scutellariae Radix*, 4-8 parts by weight of *Gardeniae Fructus*, 1-5 parts by weight of *Angelicae Sinensis Radix*, 1-5 parts by weight of *Rehmanniae radix*, 1-5 parts by weight of *Akebiae Caulis*, 1-5 parts by weight of *Bupleurum chinense*, 1-5 parts by weight of *Plantaginis Semen*, 2-6 parts by weight of *Atractylodes lancea*, 7-11 parts by weight of *Rhizoma alismatis*, 3-7 parts by weight of *Glycyrrhiza uralensis*, and 3-7 parts by weight of *Typhae pollen*. Preferably, the first mixture may comprise 2-4 parts by weight of *Gentiana scabra*, 2-4 parts by weight of *Scutellariae Radix*, 5-7 parts by weight of *Gardeniae Fructus*, 2-4 parts by weight of *Angelicae Sinensis Radix*, 2-4 parts by weight of *Rehmanniae radix*, 2-4 parts by weight of *Akebiae Caulis*, 2-4 parts by weight of *Bupleurum chinense*, 2-4 parts by weight of *Plantaginis Semen*, 3-5 parts by weight of *Atractylodes lancea*, 8-10 parts by weight of *Rhizoma alismatis*, 4-6 parts by weight of *Glycyrrhiza uralensis*, and 4-6 parts by weight of *Typhae pollen*.

In another embodiment of the present invention, the first mixture may further comprise *Moutan cortex*, *Puerariae lobatae radix*, and optionally *Rhei Radix et Rhizoma*. Preferably, the first mixture may comprise 6-10 parts by weight of *Moutan cortex*, 6-10 parts by weight of *Puerariae lobatae radix*, and 0-3 parts by weight of *Rhei Radix et Rhizoma*. More preferably, the first mixture may comprise 7-9 parts by weight of *Moutan cortex*, 7-9 parts by weight of *Puerariae lobatae radix*, and 0-2 parts by weight of *Rhei Radix et Rhizoma*.

In one aspect of the present invention, the first mixture may comprise 1-5 parts by weight of *Gentiana scabra*, 9-13 parts by weight of *Scutellariae Radix*, 1-5 parts by weight of *Gardeniae Fructus*, 1-5 parts by weight of *Angelicae Sinensis Radix*, 1-5 parts by weight of *Rehmanniae radix*, 1-5 parts by weight of *Akebiae Caulis*, 1-5 parts by weight of *Bupleurum chinense*, 1-5 parts by weight of *Plantaginis Semen*, 2-6 parts by weight of *Atractylodes lancea*, 2-6 parts by weight of *Rhizoma alismatis*, 3-7 parts by weight of *Glycyrrhiza uralensis*, 6-10 parts by weight of *Moutan cortex*, 6-10 parts by weight of *Puerariae lobatae radix*, and 0-3 parts by weight of *Rhei Radix et Rhizoma*. Preferably, the first mixture may comprise 2-4 parts by weight of *Gentiana scabra*, 10-12 parts by weight of *Scutellariae Radix*, 2-4 parts by weight of *Gardeniae Fructus*, 2-4 parts by weight of *Angelicae Sinensis Radix*, 2-4 parts by weight of *Rehmanniae radix*, 2-4 parts by weight of *Akebiae Caulis*, 2-4 parts by weight of *Bupleurum chinense*, 2-4 parts by weight of *Plantaginis Semen*, 3-5 parts by weight of *Atractylodes lancea*, 3-5 parts by weight of *Rhizoma alismatis*, 4-6 parts by weight of *Glycyrrhiza uralensis,* 7-9 parts by weight of *Moutan cortex,* 7-9 parts by weight of *Puerariae lobatae radix,* and 0-2 parts by weight of *Rhei Radix et Rhizoma.*

In another embodiment of the present invention, the first mixture may further comprise *Fructus Crataegi* and *Galli Gigerii Endothelium Coreneum.* Preferably, the first mixture may comprise 2-6 parts by weight of *Fructus Crataegi* and 2-6 parts by weight of *Galli Gigerii Endothelium Coreneum.* More preferably, the first mixture may comprise 3-5 parts by weight of *Fructus Crataegi* and 3-5 parts by weight of *Galli Gigerii Endothelium Coreneum.*

In another embodiment of the present invention, the first mixture may further comprise *Moutan cortex, Puerariae lobatae radix, Fructus Crataegi, Galli Gigerii Endothelium Coreneum,* and optionally *Rhei* Radix et *Rhizoma.* Preferably, the first mixture may comprise 1-5 parts by weight of *Gentiana scabra,* 9-13 parts by weight of *Scutellariae Radix,* 1-5 parts by weight of *Gardeniae Fructus,* 1-5 parts by weight of *Angelicae Sinensis Radix,* 1-5 parts by weight of *Rehmanniae radix,* 1-5 parts by weight of *Akebiae Caulis,* 1-5 parts by weight of *Bupleurum chinense,* 1-5 parts by weight of *Plantaginis Semen,* 2-6 parts by weight of *Atractylodes lancea,* 2-6 parts by weight of *Rhizoma alismatis,* 3-7 parts by weight of *Glycyrrhiza uralensis,* 6-10 parts by weight of *Moutan cortex,* 6-10 parts by weight of *Puerariae lobatae radix,* 0-3 parts by weight of *Rhei Radix* et *Rhizoma,* 2-6 parts by weight of *Fructus Crataegi* and 2-6 parts by weight of *Galli Gigerii Endothelium Coreneum.* More preferably, the first mixture may comprise 2-4 parts by weight of *Gentiana scabra,* 10-12 parts by weight of *Scutellariae Radix,* 2-4 parts by weight of *Gardeniae Fructus,* 2-4 parts by weight of *Angelicae Sinensis Radix,* 2-4 parts by weight of *Rehmanniae radix,* 2-4 parts by weight of *Akebiae Caulis,* 2-4 parts by weight of *Bupleurum chinense,* 2-4 parts by weight of *Plantaginis Semen,* 3-5 parts by weight of *Atractylodes lancea,* 3-5 parts by weight of *Rhizoma alismatis,* 4-6 parts by weight of *Glycyrrhiza uralensis,* 7-9 parts by weight of *Moutan cortex,* 7-9 parts by weight of *Puerariae lobatae radix,* 0-2 parts by weight of *Rhei Radix* et *Rhizoma,* 3-5 parts by weight of *Fructus Crataegi* and 3-5 parts by weight of *Galli Gigerii Endothelium Coreneum.*

The Chinese medicine composition of the present invention is prepared by the following steps: providing the first mixture; mixing the first mixture with water to form a second mixture; and heating the second mixture to obtain the Chinese medicine composition.

Here, in the present invention, the part by weight may be 2.5-5 grains per part. Preferably, the part by weight is 3-4 grams per part. More preferably, the part by weight is 3.75 grams per part.

In the present invention, the bladder cancer comprises urothelial carcinoma, squamous cell carcinoma, adenocarcinoma, sarcoma, or small cell carcinoma. However, the present invention is not limited thereto. In the present invention, the term "side effect" comprises red and swollen bladder lining, pollakiuria, hematuria, dysuria, poor appetite, frigophobia, pain and the like. However, the present invention is not limited thereto.

The present invention is not restrictive of the method for heating the Chinese medicine, and it can be implemented by any known method, such as direct heating and double-boiling.

In the present invention, the term "treat" or "treatment" used herein includes ameliorating, alleviating, or improving related symptoms, or inhibiting or controlling the progression of the disease. However, the present invention is not limited thereto.

In the present invention, the term "effective amount" used herein refers to a necessary dose leading to expected therapeutic effects in a subject treated, and it may be changed depending on the route of administration, the use of excipients and the combined use with other medicaments.

The Chinese medicine composition of the present invention may be administered via oral administration or injection.

The Chinese medicine composition of the present invention may further comprise pharmaceutically acceptable carrier, stabilizer, diluent, dispersant, suspending agents, thickening agent, excipient, or the combination thereof.

In the present invention, the term "acceptable" used herein refers to that it should be compatible with the Chinese medicine composition, preferably be able to stabilize the Chinese medicine composition, and cannot jeopardize the subject treated.

The present invention achieve the object of treating a side effect caused by bacillus Calmette-Guérin (BCG) perfusion therapy for bladder cancer, by administering a specific Chinese medicine composition to a subject in need thereof.

DETAILED DESCRIPTION OF THE PREFERRED EMBODIMENT

The following embodiments are meant to explain the implementation of the present invention, they should be construed as descriptive merely, and should not restrict the remaining part of the present invention. The person having ordinary skills in the art can easily understand other advantages and effects of the present invention. The present invention may also be implemented or applied by other different embodiments, and various details in this specification may also be modified and changed according to different viewpoints and applications without departing from the spirit of the invention.

In addition, ordinal numbers such as "first", "second" and the like used in the specification and claim for modifying elements of the claim do not mean and represent the claimed elements have any antecedent ordinal number, nor do they represent the order (or order of production) between a claimed element and another claimed element. The ordinal numbers are only used to clearly distinguish certain claimed elements having the same name.

The preparation of the Chinese medicine composition of the present invention is described below, wherein the materials used in the present invention are commercially available and easy to obtain. In addition, the part by weight is 3.75 grains per part.

Preparation Example 1: Preparation of Chinese Medicine Composition-1

Provide 3 parts by weight of *Gentiana scabra,* 3 parts by weight of *Scutellariae Radix,* 6 parts by weight of *Gardeniae Fructus,* 3 parts by weight of *Angelicae Sinensis Radix,* 3 parts by weight of *Rehmanniae radix,* 3 parts by weight of *Akebiae Caulis,* 3 parts by weight of *Bupleurum chinense,* 3 parts by weight of *Plantaginis Semen,* 4 parts by weight of *Atractylodes lancea,* 9 parts by weight of *Rhizoma alismatis,* 5 parts by weight of *Glycyrrhiza uralensis,* and 5 parts by weight of *Typhae pollen* to form a first mixture-1; mix the first mixture-1 with about 267 parts by weight of water to form a second mixture-1; heat the second mixture-1 for about 1 hour; filter the crude extract to remove a residue and obtain a Chinese medicine composition-1.

Preparation Example 2: Preparation of Chinese Medicine Composition-2

Provide 3 parts by weight of *Gentiana scabra*, 11 parts by weight of *Scutellariae Radix*, 6 parts by weight of *Gardeniae Fructus*, 3 parts by weight of *Angelicae Sinensis Radix*, 3 parts by weight of *Rehmanniae radix*, 3 parts by weight of *Akebiae Caulis*, 3 parts by weight of *Bupleurum chinense*, 3 parts by weight of *Plantaginis Semen*, 4 parts by weight of *Atractylodes lancea*, 4 parts by weight of *Rhizoma alismatis*, 5 parts by weight of *Glycyrrhiza uralensis*, 8 parts by weight of *Moutan cortex*, 8 parts by weight of *Puerariae lobatae radix*, and 0.5 parts by weight of *Rhei Radix* et *Rhizoma* to form a first mixture-2; mix the first mixture-2 with about 267 parts by weight of water to form a second mixture-2; heat the second mixture-2 to form about 120 parts by weight of a crude extract; filter the crude extract to remove a residue and obtain a Chinese medicine composition-2.

Preparation Example 3: Preparation of Chinese Medicine Composition-3

Provide 3 parts by weight of *Gentiana scabra*, 11 parts by weight of *Scutellariae Radix*, 6 parts by weight of *Gardeniae Fructus*, 3 parts by weight of *Angelicae Sinensis Radix*, 3 parts by weight of *Rehmanniae radix*, 3 parts by weight of *Akebiae Caulis*, 3 parts by weight of *Bupleurum chinense*, 3 parts by weight of *Plantaginis Semen*, 4 parts by weight of *Atractylodes lancea*, 4 parts by weight of *Rhizoma alismatis*, 5 parts by weight of *Glycyrrhiza uralensis*, 8 parts by weight of *Moutan cortex*, 8 parts by weight of *Puerariae lobatae radix*, 0.5 parts by weight of *Rhei Radix* et *Rhizoma*, 4 parts by weight of *Fructus Crataegi* and 4 parts by weight of *Galli Gigerii Endothelium Coreneum* to form a first mixture-3; mix the first mixture-3 with about 267 parts by weight of water to form a second mixture-3; heat the second mixture-3 to form about 120 parts by weight of a crude extract; filter the crude extract to remove a residue and obtain a Chinese medicine composition-3.

Embodiment 1

Due to bladder cancer, a 32-year-old male patient of Example 1 was performed with tumor curettage followed by BCG perfusion therapy. After two months of the BCG perfusion therapy, red and swollen bladder lining was observed in the patient by cystoscopic examination, and the patient had conditions of pollakiuria and dysuria.

A treatment of the present invention applied to the patient of Example 1 was described below. A daily dose of the Chinese medicine composition-1 was administered to the patient every day, wherein the daily dose of the Chinese medicine composition-1 was divided into aliquots for ter in die administration. After taking the Chinese medicine composition-1 for a month, the conditions of pollakiuria and dysuria were no longer observed. In addition, after follow-up for more than 20 years, no recurrence of dysuria or bladder cancer was found, and the tumor metastasis to the ureter or kidney was not found.

Embodiment 2

Due to bladder cancer, a male patient of Example 2 was performed with tumor curettage, and had conditions of hematuria, losing control of urination, and frigophobia. Later, BCG perfusion therapy was performed on the patient.

A treatment of the present invention applied to the patient of Example 2 was described below. After the tumor curettage was performed, a daily dose of the Chinese medicine composition-2 was administered to the patient every day, wherein the daily dose of the Chinese medicine composition-2 was divided into aliquots for ter in die administration. After taking the Chinese medicine composition-2 for three weeks, the conditions including frigophobia were no longer observed. In addition, the patient of Example 2 not only took the Chinese medicine composition-2 before receiving the BCG perfusion therapy, but also daily took the Chinese medicine composition-2 during the course of BCG perfusion therapy. Therefore, the patient had no uncomfortable reaction during the course BCG perfusion therapy.

Embodiment 3

In the Embodiment 3, an 82-year-old male patient had four tumors with a total size of 6.5 cm in the bladder, and the tumors were scraped by endoscope. Later, BCG perfusion therapy was performed. During the course of the treatment above, the patient had conditions of hematuria, pain and poor appetite.

A treatment of the present invention applied to the patient of Example 3 was described below. After the tumor curettage was performed, a daily dose of the Chinese medicine composition-2 was administered to the patient every day, wherein the daily dose of the Chinese medicine composition-2 was divided into aliquots for ter in die administration. After taking the Chinese medicine composition-2 for three months, the patient still had conditions of pain and poor appetite. Then, the Chinese medicine composition-3 was administered to the patient every day instead, wherein the daily dose of the Chinese medicine composition-3 was divided into aliquots for ter in die administration. After about 3 months, bladder endoscopy was performed, no new tumor was found, and the side effects were significantly improved. After 9 years of follow-up, the bladder tumor did not recur or metastasized.

Although the present invention has been explained in relation to its preferred embodiment, it is to be understood that many other possible modifications and variations can be made without departing from the spirit and scope of the invention as hereinafter claimed.

What is claimed is:

1. A method for treating a side effect caused by bacillus Calmette-Guérin (BCG) perfusion therapy for bladder cancer, comprising:
    administering a Chinese medicine composition to a subject in need thereof;
    wherein, the Chinese medicine composition is an extract of a first mixture consisting of *Gentiana scabra, Scutellariae Radix, Gardeniae Fructus, Angelicae Sinensis Radix, Rehmanniae radix, Akebiae Caulis, Bupleurum chinense, Plantaginis Semen, Atractylodes lancea, Rhizoma alismatis, Glycyrrhiza uralensis*, and *Typhae pollen*.

2. The method of claim 1, wherein the Chinese medicine composition is prepared by the following steps:
    providing the first mixture;
    mixing the first mixture with water to form a second mixture; and
    heating the second mixture to obtain the Chinese medicine composition.

3. The method of claim 1, wherein the first mixture consists of 1-5 parts by weight of *Gentiana scabra*, 1-13 parts by weight of *Scutellariae Radix*, 1-8 parts by weight of *Gardeniae Fructus*, 1-5 parts by weight of *Angelicae Sinensis Radix*, 1-5 parts by weight of *Rehmanniae radix*, 1-5 parts by weight of *Akebiae Caulis*, 1-5 parts by weight of *Bupleurum chinense*, 1-5 parts by weight of *Plantaginis Semen*, 2-6 parts by weight of *Atractylodes lancea*, 2-11 parts by weight of *Rhizoma alismatis*, 3-7 parts by weight of *Glycyrrhiza uralensi*, and *Typhae pollen*.

4. The method of claim 3, wherein the first mixture consists of 2-4 parts by weight of *Gentiana scabra*, 2-12 parts by weight of *Scutellariae Radix*, 2-7 parts by weight of *Gardeniae Fructus*, 2-4 parts by weight of *Angelicae Sinensis Radix*, 2-4 parts by weight of *Rehmanniae radix*, 2-4 parts by weight of *Akebiae Caulis*, 2-4 parts by weight of *Bupleurum chinense*, 2-4 parts by weight of *Plantaginis Semen*, 3-5 parts by weight of *Atractylodes lancea*, 3-10 parts by weight of *Rhizoma alismatis*, 4-6 parts by weight of *Glycyrrhiza uralensis*, and 3-7 parts by weight of *Typhae pollen*.

5. The method of claim 3, wherein each of the parts by weight is 2.5-5 grams per part.

6. A method for treating a side effect caused by bacillus Calmette-Guérin (BCG) perfusion therapy for bladder cancer, comprising:
   administering a Chinese medicine composition to a subject in need thereof,
   wherein, the Chinese medicine composition is an extract of a first mixture consisting of *Gentiana scabra, Scutellariae Radix, Gardeniae Fructus, Angelicae Sinensis Radix, Rehmanniae radix, Akebiae Caulis, Bupleurum chinense, Plantaginis Semen, Atractylodes lancea, Rhizoma alismatis, Glycyrrhiza uralensis, Moutan cortex, Puerariae lobatae radix*, and optionally *Rhei Radix* et *Rhizoma*.

7. The method of claim 6, wherein the first mixture consists of 1-5 parts by weight of *Gentiana scabra*, 9-13 parts by weight of *Scutellariae Radix*, 1-5 parts by weight of *Gardeniae Fructus*, 1-5 parts by weight of *Angelicae Sinensis Radix*, 1-5 parts by weight of *Rehmanniae radix*, 1-5 parts by weight of *Akebiae Caulis*, 1-5 parts by weight of *Bupleurum chinense*, 1-5 parts by weight of *Plantaginis Semen*, 2-6 parts by weight of *Atractylodes lancea*, 2-6 parts by weight of *Rhizoma alismatis*, 3-7 parts by weight of *Glycyrrhiza uralensis*, 6-10 parts by weight of *Moutan cortex*, 6-10 parts by weight of *Puerariae lobatae radix*, and 0-3 parts by weight of *Rhei Radix* et *Rhizoma*.

8. The method of claim 7, wherein the first mixture consists of 2-4 parts by weight of *Gentiana scabra*, 10-12 parts by weight of *Scutellariae Radix*, 2-4 parts by weight of *Gardeniae Fructus*, 2-4 parts by weight of *Angelicae Sinensis Radix*, 2-4 parts by weight of *Rehmanniae radix*, 2-4 parts by weight of *Akebiae Caulis*, 2-4 parts by weight of *Bupleurum chinense*, 2-4 parts by weight of *Plantaginis Semen*, 3-5 parts by weight of *Atractylodes lancea*, 3-5 parts by weight of *Rhizoma alismatis*, 4-6 parts by weight of *Glycyrrhiza uralensis*, 7-9 parts by weight of *Moutan cortex*, 7-9 parts by weight of *Puerariae lobatae radix*, and 0-2 parts by weight of *Rhei Radix* et *Rhizoma*.

9. A method for treating a side effect caused by bacillus Calmette-Guérin (BCG) perfusion therapy for bladder cancer, comprising:
   administering a Chinese medicine composition to a subject in need thereof,
   wherein, the Chinese medicine composition is an extract of a first mixture consisting of *Gentiana scabra, Scutellariae Radix, Gardeniae Fructus, Angelicae Sinensis Radix, Rehmanniae radix, Akebiae Caulis, Bupleurum chinense, Plantaginis Semen, Atractylodes lancea, Rhizoma alismatis, Glycyrrhiza uralensis, Moutan cortex, Puerariae lobatae radix*, optionally *Rhei Radix* et *Rhizoma, Fructus Crataegi* and *Galli Gigerii Endothelium Coreneum*.

10. The method of claim 9, wherein the first mixture consists of 1-5 parts by weight of *Gentiana scabra*, 9-13 parts by weight of *Scutellariae Radix*, 1-5 parts by weight of *Gardeniae Fructus*, 1-5 parts by weight of *Angelicae Sinensis Radix*, 1-5 parts by weight of *Rehmanniae radix*, 1-5 parts by weight of *Akebiae Caulis*, 1-5 parts by weight of *Bupleurum chinense*, 1-5 parts by weight of *Plantaginis Semen*, 2-6 parts by weight of *Atractylodes lancea*, 2-6 parts by weight of *Rhizoma alismatis*, 3-7 parts by weight of *Glycyrrhiza uralensis*, 6-10 parts by weight of *Moutan cortex*, 6-10 parts by weight of *Puerariae lobatae radix*, 0-3 parts by weight of *Rhei Radix* et *Rhizoma*, 2-6 parts by weight of *Fructus Crataegi* and 2-6 parts by weight of *Galli Gigerii Endothelium Coreneum*.

11. The method of claim 10, wherein the first mixture consists of 2-4 parts by weight of *Gentiana scabra*, 10-12 parts by weight of *Scutellariae Radix*, 2-4 parts by weight of *Gardeniae Fructus*, 2-4 parts by weight of *Angelicae Sinensis Radix*, 2-4 parts by weight of *Rehmanniae radix*, 2-4 parts by weight of *Akebiae Caulis*, 2-4 parts by weight of *Bupleurum chinense*, 2-4 parts by weight of *Plantaginis Semen*, 3-5 parts by weight of *Atractylodes lancea*, 3-5 parts by weight of *Rhizoma alismatis*, 4-6 parts by weight of *Glycyrrhiza uralensis*, 7-9 parts by weight of *Moutan cortex*, 7-9 parts by weight of *Puerariae lobatae radix*, 0-2 parts by weight of *Rhei Radix* et *Rhizoma*, 3-5 parts by weight of *Fructus Crataegi* and 3-5 parts by weight of *Galli Gigerii Endothelium Coreneum*.

12. The method of claim 1, wherein the bladder cancer comprises urothelial carcinoma, squamous cell carcinoma, adenocarcinoma, sarcoma, or small cell carcinoma.

13. The method of claim 1, wherein the side effect comprises red and swollen bladder lining, pollakiuria, hematuria, dysuria, poor appetite, frigophobia or pain.

14. The method of claim 6, wherein the Chinese medicine composition is prepared by the following steps:
   providing the first mixture;
   mixing the first mixture with water to form a second mixture; and
   heating the second mixture to obtain the Chinese medicine composition.

15. The method of claim 7, wherein each of the parts by weight is 2.5-5 grams per part.

16. The method of claim 9, wherein the Chinese medicine composition is prepared by the following steps:
   providing the first mixture;
   mixing the first mixture with water to form a second mixture; and
   heating the second mixture to obtain the Chinese medicine composition.

17. The method of claim 10, wherein each of the parts by weight is 2.5-5 grams per part.

18. The method of claim 6, wherein the bladder cancer comprises urothelial carcinoma, squamous cell carcinoma, adenocarcinoma, sarcoma, or small cell carcinoma.

19. The method of claim 6, wherein the side effect comprises red and swollen bladder lining, pollakiuria, hematuria, dysuria, poor appetite, frigophobia or pain.

20. The method of claim 9, wherein the bladder cancer comprises urothelial carcinoma, squamous cell carcinoma, adenocarcinoma, sarcoma, or small cell carcinoma.

21. The method of claim 9, wherein the side effect comprises red and swollen bladder lining, pollakiuria, hematuria, dysuria, poor appetite, frigophobia or pain.

\* \* \* \* \*